(12) United States Patent
Grasso et al.

(10) Patent No.: US 7,332,584 B2
(45) Date of Patent: Feb. 19, 2008

(54) ANTIBODIES THAT SPECIFICALLY BIND PMS2

(75) Inventors: Luigi Grasso, Bala Cynwyd, PA (US); Nicholas C. Nicolaides, Boothwyn, PA (US); Philip M. Sass, Audubon, PA (US); Eric Routhier, Glen Mills, PA (US)

(73) Assignee: Morphotek, Inc., Exton, PA (US)

( * ) Notice: Subject to any disclaimer, the term of this patent is extended or adjusted under 35 U.S.C. 154(b) by 0 days.

(21) Appl. No.: 11/007,428

(22) Filed: Dec. 8, 2004

(65) Prior Publication Data

US 2006/0009621 A1 Jan. 12, 2006

Related U.S. Application Data

(60) Provisional application No. 60/528,269, filed on Dec. 8, 2003.

(51) Int. Cl.
*C07K 16/00* (2006.01)
*C12P 21/08* (2006.01)

(52) U.S. Cl. .................... 530/388.1; 530/530

(58) Field of Classification Search .............. 530/387.1
See application file for complete search history.

(56) References Cited

U.S. PATENT DOCUMENTS

| | | | |
|---|---|---|---|
| 4,694,778 A | 9/1987 | Learn et al. | 118/728 |
| 5,789,650 A | 8/1998 | Lonberg et al. | 800/18 |
| 5,798,230 A | 8/1998 | Bornkamm et al. | 435/70.21 |
| 6,146,894 A * | 11/2000 | Nicolaides et al. | 435/440 |
| 6,191,268 B1 | 2/2001 | Liskay et al. | 536/23.5 |
| 6,416,984 B1 | 7/2002 | Haseltine et al. | 435/183 |

FOREIGN PATENT DOCUMENTS

| | | |
|---|---|---|
| EP | 0 239 400 | 9/1987 |
| WO | WO 90/07861 | 7/1990 |
| WO | WO 96/41192 A1 | 12/1996 |
| WO | WO 02/054856 | 7/2002 |

OTHER PUBLICATIONS

Kricka and Wild (The Immunoassay Handbook, second edition, 2001, pp. 159-176).*
Riechmann, L., et al., "Reshaping human antibodies for therapy," *Nature*, 1988, 332, 323-327.
Verhoeyen, M., et al., "Reshaping human antibodies: grafting an antilysozyme activity," *Science*, 1988, 239, 1534-1536.
Khazaeli, M.B., et al., "Human immune response to monoclonal antibodies," *J. of Immunother.*, 1994, 15, 42-52.
Jones, P.T., et al., "replacing the complementarity-determining regions in a human antibody with those from a mouse," *Nature*, 1986, 321, 522-525.
Orlandi, R., et al., "Cloning immunoglobulin variable domains for expression by the polymerase chain reaction," *Proc. Natl. Acad. Sci. USA*, 1989, 86, 3833-3837.
Queen, C., et al., "A humanized antibody that binds to the interleukin 2 receptor," *Proc. Natl. Acad. Sci. USA*, 1989, 86, 10029-10033.
Tempest, P.R., et al., "Reshaping a human monoclonal antibody to inhibit human respiratory syncytial virus infection in vivo," *Biotechnology*, 1991, 9, 266-271.
Bird, R.E., "Single-chain antigen-binding proteins," Science, 1988, 242, 423-442.
Huston, J.S., et al., "Protein engineering of antibody binding sites: recovery of specific activity in an anti-digoxin single-chain Fv analogue produced in *Escherichia coli,*" *Proc. Natl. Acad. Sci. USA*, 1988, 85, 5879-5883.
Ward, E.S., et al., "Binding activities of a repertoire of single immunoglobulin variable domains," *Nature*, 1989, 334, 544-546.
Skerra, A., et al., "Assembly of a functional immunoglobulin $F_v$ fragment in *Escherichia coli,*" *Science*, 1988, 242, 1038-1041.
Kohler G., et al., "Continuous cultures of fused cells secreting antibody of predefined specificity," *Nature*, 1995, 256, 495-497.
Kozbor, D., et al., "The production of monoclonal antibodies from human lymphocytes," *Immunol. Today*, 1983, 4(3), 72-79.
Cole, S.P.C., et al., "The EBV-hybridoma technique and its application to human lung cancer," *Monoclonal Antibodies and Cancer Therapy*, Alan R. Liss, Inc., 1985, 77-96.
Boerner, P., et al., "Production of antigen-specific human monoclonal antibodies from in vitro-primed human splenocytes," *J. of Immunol.*, 1991, 147(1), 86-95.
Persson, M.A.A., et al., "Generation of diverse high-affinity human monoclonal antibodies by repertoire cloning," *Proc. Nat. Acad. Sci. USA*, 1991, 88, 2432-2436.
Huang, X., et al., "On global sequence alignment," CABIOS, 1994, 10(3), 227-235.
Zafiropoulos, A., et al., "Induction of antigen-specific isotype switching by in vitro immunization of human naïve B lymphocytes," *J. of Immunological Methods*, 1997, 200, 181-190.
BD Pharmingen Technical Data Sheet, "Purified mouse Anti-PMS2 monoclonal antibody," *BD Biosciences*, 2004, Catalog No. 556415, 1 page.
Manavis, J., et al., "The immunohistochemical detection of mismatch repair gene proteins (MLH1, MSH2, MSH6, and PMS2): practical aspects in antigen retrieval and biotin blocking protocols," *Appl. Immunohistochemistry & Molecular Morphology*, 2003, 11(1), 73-77.
Nicolaides, N.C., et al., "A naturally occurring *hPMS2* mutation can confer a dominant negative mutator phenotype," *Molecular & Cellular Biol.*, 1998, 18(3), 1635-1641.

* cited by examiner

*Primary Examiner*—Misook Yu
*Assistant Examiner*—Sean E Aeder
(74) *Attorney, Agent, or Firm*—Woodcock Washburn LLP

(57) ABSTRACT

Antibodies against PMS2 and PMS2-134 and cells that produce the anti-PMS2 and anti-PMS2-134 antibodies are provided. The antibodies of the invention may be used in methods for detecting a PMS2 protein, including a truncated PMS2, and in methods for detecting an abnormal condition in a patient.

8 Claims, 1 Drawing Sheet

ANTIBODIES THAT SPECIFICALLY BIND PMS2

CROSS-REFERENCE TO RELATED APPLICATIONS

This claims benefit of U.S. Provisional Application Ser. No. 60/528,269, filed Dec. 8, 2003, the entire contents of which is incorporated herein by reference.

FIELD OF THE INVENTION

The invention relates to antibodies against PMS2 and cells that produce the anti-PMS2 antibodies. The invention also relates to methods for detecting a PMS2 protein and methods for detecting an abnormal condition in a patient using the antibodies of the invention.

BACKGROUND OF THE INVENTION

PMS2 is a protein involved in mismatch repair (MMR). The process of MMR, also called mismatch proofreading, is carried out by protein complexes in cells ranging from bacteria to mammalian cells. A MMR gene is a gene that encodes for one of the proteins of such a mismatch repair complex. The MMR complex is believed to detect distortions of the DNA helix resulting from non-complementary pairing of nucleotide bases. The non-complementary base on the newer DNA strand is excised, and the excised base is replaced with the appropriate base, which is complementary to the older DNA strand. In this way, cells eliminate many mutations that occur as a result of mistakes in DNA replication.

Dominant negative alleles of mismatch repair genes have been shown to cause a MMR-defective phenotype even in the presence of a wild-type allele in the same cell. An example of a dominant negative allele of a MMR gene is the human gene hPMS2-134, which carries a truncating mutation at codon 134. The mutation causes the product of this gene to abnormally terminate at the position of the 134th amino acid, resulting in a shortened polypeptide containing the N-terminal 133 amino acids. Such a mutation causes an increase in the rate of mutations, which accumulate in cells after DNA replication. Expression of a dominant negative allele of a mismatch repair gene results in impairment of mismatch repair activity, even in the presence of the wild-type allele. Any allele which produces such effect can be used in this invention. Dominant negative alleles of a MMR gene can be obtained from the cells of humans, animals, yeast, bacteria, or other organisms.

Antibodies to detect PMS2 and truncation mutants thereof would be useful in biological assays for studying mismatch repair, and in diagnostic applications for detecting the presence of a form of PMS2 which may predispose a patient to cancer.

SUMMARY OF THE INVENTION

The invention relates to novel antibodies that specifically bind PMS2. The antibodies specifically recognize a portion of the amino-terminal portion of PMS2, such that truncation mutants of PMS2 may also be detected.

The antibodies of the invention may be used in immunological assays to detect the presence of PMS2 in a sample. The methods may also be used to detect truncated forms of PMS2. Such assays include, but are not limited to radioimmunoassay, Western blot, ELISA, immunoprecipitation, and the like.

The antibodies of the invention may be used in a method for detecting a predisposition to cancer in a patient, wherein a truncated form of PMS2 is detected in a patient sample in a screening assay and correlated to a risk of cancer in the patient.

DETAILED DESCRIPTION OF ILLUSTRATIVE EMBODIMENTS

Figure 1:
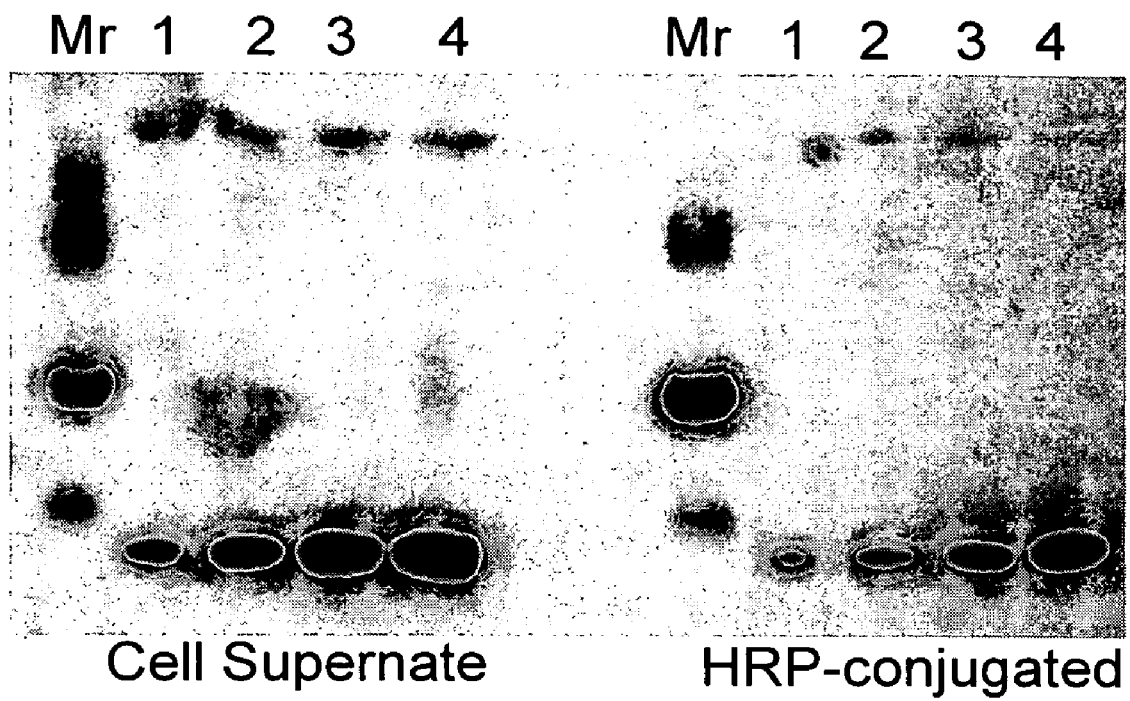
FIG. 1 shows reactivity in a Western blot of antibody from a 349-29.5.2 cell supernate and an HRP-conjugated purified antibody from 349-29.5.2 against human PMS2-134 expressed in a human cell line.

The reference works, patents, patent applications, and scientific literature, including accession numbers to GenBank database sequences that are referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

Standard reference works setting forth the general principles of recombinant DNA technology known to those of skill in the art include Ausubel et al., CURRENT PROTOCOLS IN MOLECULAR BIOLOGY, John Wiley & Sons, New York (1998); Sambrook et al., MOLECULAR CLONING: A LABORATORY MANUAL, 2D ED., Cold Spring Harbor Laboratory Press, Plainview, N.Y. (1989); Kaufman et al., Eds., HANDBOOK OF MOLECULAR AND CELLULAR METHODS IN BIOLOGY AND MEDICINE, CRC Press, Boca Raton (1995); McPherson, Ed., DIRECTED MUTAGENESIS: A PRACTICAL APPROACH, IRL Press, Oxford (1991).

As used herein, the term "epitope" refers to the portion of an antigen to which a monoclonal antibody specifically binds.

As used herein, the term "conformational epitope" refers to a discontinuous epitope formed by a spatial relationship between amino acids of an antigen other than an unbroken series of amino acids.

As used herein, the term "about" refers to an approximation of a stated value within an acceptable range. Preferably the range is +/−5% of the stated value.

The antibodies of the invention specifically bind to PMS2 and truncated fragments thereof. The antibodies include those in which the epitope is found within the amino acid sequence of SEQ ID NO:1 or SEQ ID NO:2. In other embodiments, the epitope comprises the sequence of SEQ ID NO:1 or SEQ ID NO:2. In specific embodiments, the antibody is 349-22.1.3. In other embodiments, the antibody is 349-29.5.2.

In some embodiments the antibody is produced in a host cell other than a hybridoma cell. In these cases the antibody genes are cloned out of the hybridomas 349.22.1.3 and/or 349-29.5.2 and placed in an expression vector, operably linked to expression control sequences such that a functional antibody is produced.

Preferred antibodies and antibodies suitable for use in the methods of the invention include, for example, fully human antibodies, human antibody homologs, humanized antibody homologs, chimeric antibody homologs, Fab, Fab', F(ab')$_2$ and F(v) antibody fragments, single chain antibodies, and monomers or dimers of antibody heavy or light chains or mixtures thereof.

The antibodies of the invention may include intact immunoglobulins of any isotype including types IgA, IgG, IgE, IgD, IgM (as well as subtypes thereof). The light chains of the immunoglobulin may be kappa or lambda. Class switching may be induced or may be engineered through recombinant techniques known in the art using the antibodies expressed in the hybridoma cells 349-22.1.3 and 349-29.5.2.

The antibodies of the invention include portions of intact antibodies that retain antigen-binding specificity, for example, Fab fragments, Fab' fragments, F(ab')$_2$ fragments, F(v) fragments, heavy chain monomers or dimers, light chain monomers or dimers, dimers consisting of one heavy and one light chain, and the like. Thus, antigen-binding fragments as well as full-length dimeric or trimeric polypeptides derived from the above-described antibodies are themselves useful.

The expression cells of the invention include any insect expression cell line known, such as, for example, *Spodoptera frugiperda* cells. The expression cell lines may also be bacterial or fungal cell lines. The expression cell lines also may be yeast cell lines, such as, for example, *Saccharomyces cerevisiae* and *Schizosaccharomyces pombe* cells. The expression cells may also be mammalian cells such as, for example, Chinese hamster ovary, baby hamster kidney cells, human embryonic kidney line 293, normal dog kidney cell lines, normal cat kidney cell lines, monkey kidney cells, African green monkey kidney cells, COS cells, and non-tumorigenic mouse myoblast G8 cells, fibroblast cell lines, myeloma cell lines, mouse NIH/3T3 cells, LMTK31 cells, mouse sertoli cells, human cervical carcinoma cells, buffalo rat liver cells, human lung cells, human liver cells, mouse mammary tumor cells, TR1 cells, MRC 5 cells, and FS4 cells.

A "chimeric antibody" is an antibody produced by recombinant DNA technology in which all or part of the hinge and constant regions of an immunoglobulin light chain, heavy chain, or both, have been substituted for the corresponding regions from another animal's immunoglobulin light chain or heavy chain. In this way, the antigen-binding portion of the parent monoclonal antibody is grafted onto the backbone of another species' antibody. One approach, described in EP 0239400 to Winter et al., describes the substitution of one species' complementarity determining regions (CDRs) for those of another species, such as substituting the CDRs from human heavy and light chain immunoglobulin variable region domains with CDRs from mouse variable region domains. These altered antibodies may subsequently be combined with human immunoglobulin constant regions to form antibodies that are human except for the substituted murine CDRs which are specific for the antigen. Methods for grafting CDR regions of antibodies may be found, for example in Riechmann et al. (1988) *Nature* 332:323-327 and Verhoeyen et al. (1988) *Science* 239:1534-1536.

Chimeric antibodies were thought to circumvent the problem of eliciting an immune response in humans as chimeric antibodies contain less murine amino acid sequence. It was found that the direct use of rodent monoclonal antibodies (MAbs) as human therapeutic agents led to human antirodent antibody ("HARA") responses which occurred in a significant number of patients treated with the rodent-derived antibody (Khazaeli, et al., (1994) *Immunother.* 15:42-52).

As a non-limiting example, a method of performing CDR grafting may be performed by sequencing the mouse heavy and light chains of the antibody of interest that binds to the target antigen (e.g., PMS2), genetically engineering the CDR DNA sequences, and imposing these amino acid sequences to corresponding human V regions by site-directed mutagenesis. Human constant region gene segments of the desired isotype are added, and the "humanized" heavy and light chain genes are co-expressed in mammalian cells to produce soluble humanized antibody. A typical expression cell is a Chinese Hamster Ovary (CHO) cell. Suitable methods for creating the chimeric antibodies may be found, for example, in Jones et al. (1986) *Nature* 321:522-525; Riechmann (1988) *Nature* 332:323-327; Queen et al. (1989) *Proc. Nat. Acad. Sci. USA* 86:10029; and Orlandi et al. (1989) *Proc. Natl. Acad. Sci. USA* 86:3833.

Further refinement of antibodies to avoid the problem of HARA responses led to the development of "humanized antibodies." Humanized antibodies are produced by recombinant DNA technology, in which at least one of the amino acids of a human immunoglobulin light or heavy chain that is not required for antigen binding has been substituted for the corresponding amino acid from a nonhuman mammalian immunoglobulin light or heavy chain. For example, if the immunoglobulin is a mouse monoclonal antibody, at least one amino acid that is not required for antigen binding is substituted using the amino acid that is present on a corresponding human antibody in that position. Without wishing to be bound by any particular theory of operation, it is believed that the "humanization" of the monoclonal antibody inhibits human immunological reactivity against the foreign immunoglobulin molecule.

Queen et al. (1989) *Proc. Nat. Acad. Sci. USA* 86:10029-10033 and WO 90/07861 describe the preparation of a humanized antibody. Human and mouse variable framework regions were chosen for optimal protein sequence homology. The tertiary structure of the murine variable region was computer-modeled and superimposed on the homologous human framework to show optimal interaction of amino acid residues with the mouse CDRs. This led to the development of antibodies with improved binding affinity for antigen (which is typically decreased upon making CDR-grafted chimeric antibodies). Alternative approaches to making humanized antibodies are known in the art and are described, for example, in Tempest (1991) *Biotechnology* 9:266-271.

"Single chain antibodies" refer to antibodies formed by recombinant DNA techniques in which immunoglobulin heavy and light chain fragments are linked to the F(v) region via an engineered span of amino acids. Various methods of generating single chain antibodies are known, including those described in U.S. Pat. No. 4,694,778; Bird (1988) *Science* 242:423-442; Huston et al. (1988) *Proc. Natl. Acad. Sci. USA* 85:5879-5883; Ward et al. -(1989) *Nature* 334: 54454; and Skerra et al. (1988) *Science* 242:1038-1041.

The antibodies of the invention may be used alone or as immunoconjugates with a label. Such labels include enzymes, biotin, radionuclides, fluorophores, chemiluminescers, paramagnetic particles, and the like. Suitable labels include, but are not limited to fluorescein, rhodamine, isothiocyanate, phycoerythrin, horseradish peroxidase, and colloidal gold.

The antibodies of the invention include derivatives that are modified, e.g., by the covalent attachment of any type of molecule to the antibody such that covalent attachment does not prevent the antibody from binding to its epitope. Examples of suitable derivatives include, but are not limited to glycosyled antibodies and fragments, acetyled antibodies and fragments, pegylated antibodies and fragments, phosphorylated antibodies and fragments, and amidated antibodies and fragments. The antibodies and derivatives thereof of the invention may be derivatized by known protecting/blocking groups, proteolytic cleavage, linkage to a cellular ligand or other proteins, and the like. Further, the antibodies and derivatives thereof of the invention may contain one or more non-classical amino acids.

The monoclonal antibodies of the invention may be produced by immunizing animals with PMS2, truncated fragments thereof, or peptide fragments thereof. Animals so immunized will produce antibodies against the protein. Standard methods are known for creating monoclonal antibodies including, but are not limited to, the hybridoma technique (see Kohler & Milstein (1975) *Nature* 256:495-497); the trioma technique; the human B-cell hybridoma technique (see Kozbor et al. (1983) *Immunol. Today* 4:72) and the EBV hybridoma technique to produce human monoclonal antibodies (see Cole, et al. in MONOCLONAL ANTIBODIES AND CANCER THERAPY, Alan R. Liss, Inc., 1985, pp. 77-96).

Screening for antibodies that specifically bind to PMS2 or truncated fragments thereof may be accomplished using an enzyme-linked immunosorbent assay (ELISA) in which microtiter plates are coated with the PMS2, for example.

Confirmation of reactivity of the antibodies to PMS2, or truncated forms thereof may be accomplished, for example, using a Western Blot assay in which protein from normal patients or a patient with Hereditary Non-Polyposis Colon Cancer (HNPCC) are run on an SDS-PAGE gel under reducing and non-reducing conditions and subsequently are blotted onto a membrane. The membrane may then be probed with the putative anti-PMS2 antibodies. Appropriately-sized bands on Western indicates specificity of the antibodies and the ability to bind both full-length and truncated forms of PMS2.

The antibodies and derivatives thereof of the invention have binding affinities that include a dissociation constant ($K_d$) of less than $1\times10^{-2}$. In some embodiments, the $K_d$ is less than $1\times10^{-3}$. In other embodiments, the $K_d$ is less than $1\times10^{-4}$. In some embodiments, the $K_d$ is less than $1\times10^{-5}$. In still other embodiments, the $K_d$ is less than $1\times10^{-6}$. In other embodiments, the $K_d$ is less than $1\times10^{-7}$. In other embodiments, the $K_d$ is less than $1\times10^{-8}$. In other embodiments, the $K_d$ is less than $1\times10^{-9}$. In other embodiments, the $K_d$ is less than $1\times10^{-10}$. In still other embodiments, the $K_d$ is less than $1\times10^{-11}$. In some embodiments, the $K_d$ is less than $1\times10^{-12}$. In other embodiments, the $K_d$ is less than $1\times10^{-13}$. In other embodiments, the $K_d$ is less than $1\times10^{-14}$. In still other embodiments, the $K_d$ is less than $1\times10^{-15}$.

Antibodies of the invention may be produced in vivo or in vitro. For in vivo antibody production, animals are generally immunized with an immunogenic portion of PMS2 (such as an immunogenic peptide of PMS2). The antigen is generally combined with an adjuvant to promote immunogenicity. Adjuvants vary according to the species used for immunization. Examples of adjuvants include, but are not limited to: Freund's complete adjuvant ("FCA"), Freund's incomplete adjuvant ("FIA"), mineral gels (e.g., aluminum hydroxide), surface active substances (e.g., lysolecithin, pluronic polyols, polyanions), peptides, oil emulsions, keyhole limpet hemocyanin ("KLH"), dinitrophenol ("DNP"), and potentially useful human adjuvants such as Bacille Calmette-Guerin ("BCG") and *corynebacterium parvum*. Such adjuvants are also well known in the art.

Immunization may be accomplished using well-known procedures. The dose and immunization regimen will depend on the species of mammal immunized, its immune status, body weight, and/or calculated surface area, etc. Typically, blood serum is sampled from the immunized mammals and assayed for anti-PMS2 antibodies using appropriate screening assays as described below, for example.

Splenocytes from immunized animals may be immortalized by fusing the splenocytes (containing the antibody-producing B cells) with an immortal cell line such as a myeloma line. Typically, myeloma cell line is from the same species as the splenocyte donor. In one embodiment, the immortal cell line is sensitive to culture medium containing hypoxanthine, aminopterin and thymidine ("HAT medium"). In some embodiments, the myeloma cells are negative for Epstein-Barr virus (EBV) infection. In preferred embodiments, the myeloma cells are HAT-sensitive, EBV negative and Ig expression negative. Any suitable myeloma may be used. Murine hybridomas may be generated using mouse myeloma cell lines (e.g., the P3-NS1/1-Ag4-1, P3-x63-Ag8.653 or Sp2/O-Ag14 myeloma lines). These murine myeloma lines are available from the ATCC. These myeloma cells are fused to the donor splenocytes polyethylene glycol ("PEG"), preferably 1500 molecular weight polyethylene glycol ("PEG 1500"). Hybridoma cells resulting from the fusion are selected in HAT medium which kills unfused and unproductively fused myeloma cells. Unfused splenocytes die over a short period of time in culture. In some embodiments, the myeloma cells do not express immunoglobulin genes.

Hybridomas producing a desired antibody which are detected by screening assays, such as those described below, may be used to produce antibodies in culture or in animals. For example, the hybridoma cells may be cultured in a nutrient medium under conditions and for a time sufficient to allow the hybridoma cells to secrete the monoclonal antibodies into the culture medium. These techniques and culture media are well known by those skilled in the art. Alternatively, the hybridoma cells may be injected into the peritoneum of an unimmunized animal. The cells proliferate in the peritoneal cavity and secrete the antibody, which accumulates as ascites fluid. The ascites fluid may be withdrawn from the peritoneal cavity with a syringe as a rich source of the monoclonal antibody.

Another non-limiting method for producing human antibodies is described in U.S. Pat. No. 5,789,650 which describes transgenic mammals that produce antibodies of another species (e.g., humans) with their own endogenous immunoglobulin genes being inactivated. The genes for the heterologous antibodies are encoded by human immunoglobulin genes. The transgenes containing the unrearranged immunoglobulin encoding regions are introduced into a non-human animal. The resulting transgenic animals are capable of functionally rearranging the transgenic immunoglobulin sequences and producing a repertoire of antibodies of various isotypes encoded by human immunoglobulin genes. The B-cells from the transgenic animals are subsequently immortalized by any of a variety of methods, including fusion with an immortalizing cell line (e.g., a myeloma cell).

Antibodies against PMS2 may also be prepared in vitro using a variety of techniques known in the art. For example, but not by way of limitation, fully human monoclonal antibodies against PMS2 may be prepared by using in vitro-primed human splenocytes (Boerner et al. (1991) *J. Immunol.* 147:86-95).

Alternatively, for example, the antibodies of the invention may be prepared by "repertoire cloning" (Persson et al. (1991) *Proc. Nat. Acad. Sci. USA* 88:2432-2436; and Huang and Stollar (1991) *J. Immunol. Methods* 141:227-236).

Further, U.S. Pat. No. 5,798,230 describes preparation of human monoclonal antibodies from human B antibody-producing B cells that are immortalized by infection with an Epstein-Barr virus that expresses Epstein-Barr virus nuclear antigen 2 (EBNA2). EBNA2, required for immortalization, is then inactivated resulting in increased antibody titers.

In another embodiment, antibodies against PMS2 are formed by in vitro immunization of peripheral blood mononuclear cells ("PBMCs"). This may be accomplished by any means known in the art, such as, for example, using methods described in the literature (Zafiropoulos et al. (1997) *J. Immunological Methods* 200:181-190).

In one embodiment of the invention, the procedure for in vitro immunization is supplemented with directed evolution of the hybridoma cells in which a dominant negative allele of a mismatch repair gene such as PMS1, PMS2, PMS2-134, PMSR2, PMSR3, MLH1, MLH2, MLH3, MLH4, MLH5, MLH6, PMSL9, MSH1, and MSH2 is introduced into the hybridoma cells after fusion of the splenocytes, or to the myeloma cells before fusion. Cells containing the dominant negative mutant will become hypermutable and accumulate mutations at a higher rate than untransfected control cells. A pool of the mutating cells may be screened for clones that produce higher affinity antibodies, or that produce higher titers of antibodies, or that simply grow faster or better under certain conditions. The technique for generating hypermutable cells using dominant negative alleles of mismatch repair genes is described in U.S. Pat. No. 6,146,894, issued Nov. 14, 2000. Alternatively, mismatch repair may be inhibited using the chemical inhibitors of mismatch repair described by Nicolaides et al. in WO 02/054856 "Chemical Inhibitors of Mismatch Repair" published Jul. 18, 2002. The technique for enhancing antibodies using the dominant negative alleles of mismatch repair genes or chemical inhibitors of mismatch repair may be applied to mammalian expression cells expressing cloned immunoglobulin genes as well. Cells expressing the dominant negative alleles can be "cured" in that the dominant negative allele can be turned off if inducible, eliminated from the cell, and the like, such that the cells become genetically stable once more and no longer accumulate mutations at the abnormally high rate.

The immunogen may be any PMS2, however, mammalian PMS2 is preferred. Truncated forms of PMS2 may also be used. As the N-terminus of PMS2 is highly conserved across species, in some embodiments, antibodies that recognize one species of PMS2 is expected to also recognize another species. For example, but not by way of limitation, a monoclonal antibody that binds human PMS2 (SEQ ID NO:2) in the N-terminal region may also bind the same region in mouse PMS2 (SEQ ID NO:5) and even *Arabidopsis thaliana* PMS2 (SEQ ID NO:6) and in the truncated human PMS2-134 (SEQ ID NO:1). The immunogen may also be immunogenic peptides of PMS2 or highly conserved peptides of PMS2. Two such peptides that may be used are: IQEFADLTQVETFGFR (SEQ ID NO:3) and ELVENSLDAGATNIDLK (SEQ ID NO:4).

The invention also provides a method for detecting an abnormal condition in a patient expressing a truncated PMS2. The method comprises contacting a test cell lysate from the patient suspected of having a defect in mismatch repair with a monoclonal antibody secreted by hybridoma cell 349-29.5.2 or 349-22.1.3 and detecting the presence or absence of a truncated form of PMS2. The presence of a truncated form of PMS2 is indicative of an abnormal condition in mismatch repair which predisposes the patient to cancer. Such cancers include, but are not limited to hereditary non-polyposis colon cancer. The presence of the truncated form of PMS2 may be detected by various means including immunoprecipitation, western blot, and ELISA.

The following Examples are provided to illustrate the present invention, and should not be construed as limiting thereof.

EXAMPLE 1

Immunogen Expression

Five milliliters of IPTG-induced (100 mM) culture of *E. coli* BL21(DE3) cells transformed with plasmid p-ET-k-134 (a plasmid that expresses hPMS2-134 from a T7 promoter, out of frame with His tag, NB37p46) were obtained. Expression was induced by inoculation of 1 ml ($OD_{600}$=0.5) into 45 ml LB-Kan (50 mg/ml). The cells were lysed by addition of B-PER bacterial protein extraction reagent, and inclusion bodies were purified from lysates as per manufacturer's instructions. The inclusion body pellet was dissolved in 400 μl 2×LDS sample buffer, boiled 5 min, and electrophoresed 125 μl/gel, on 4 gels, of solubilized inclusion bodies in reducing 12% Bis-Tris 2-D gels in MES buffer. The gels were stained with Gelcode Blue colloidal Coomassie Blue (Pierce). Fifteen kilodalton bands were excised and sent to St. Louis University Hybridoma Facility. One gel slice was subjected to amino acid analysis. Amino acid analysis was consistent with hPMS2-134 polypeptide. Another gel slice was processed for MALDI-TOF MS analysis of trpytic peptides (NB37p72). Two peptide matches to hPMS2-134 were found upon database search (IQEFADLTQVETFGFR (SEQ ID NO:3) and ELVENSLDAGATNIDLK (SEQ ID NO:4)). For generation of hybridomas, four mice were immunized. All four were shown to be reactive to the original immunogen by Western blotting using mouse sera. Mouse #464 was chosen for lymphocyte fusion (NB70p3).

EXAMPLE 2

Cloning of a Second Bacterial Expression Construct and IMAC Purification of His-hPMS2-134

A second arabinose-inducible bacterial expression construct was made in plasmid pBAD-HisA, this time with an N-terminal 6×His tag in-frame with hPMS2-134 (NB37p1). This plasmid was designated p0126. His-tagged hPMS2-134 was purified from induced cultures of BL21 carrying p0126 by immobilized metal affinity chromatography over Talon cobalt affinity resin (Clontech, NB37p93). A single hybridoma which reacted specifically with purified hPMS2-134 (clone 349-1) was identified.

EXAMPLE 3

Screening of Murine Hybridomas and Epitope Mapping

Clone 349-1 was further subcloned by limiting dilution and screened again (NB70p8). Twelve subclones from 349-1 were tested for reactivity by Western blotting. All 12 clones were specifically reactive to bacterially produced hPMS2-134 (NB70p12). Only clone 349-1.1 was reactive towards hPMS2-134 expressed from CHO-124 or CHO-125 (CHO transfectants expressing hPMS2-134 or C-terminal V5-tagged hPMS2-134, respectively, NB70p14). A second set of three twice-subcloned hybridomas from 349-1 (349-1.2.1 through 349-1.2.3), were obtained, as well as four twice-subcloned hybridomas from 349-1 (349-1.1.1 through 349-1.1.4) and all were tested against bacterially expressed hPMS2-134. All retained reactivity against hPMS2-134. However, only clone 349-1.2.2 displayed specific reactivity towards CHO-expressed hPMS2-134. This mAb also identified a second band of Mr 120 kD from CHO lysates (putative hamster PMS2). Two hybridomas were retained from this screen (349-1.1.3 and 349-1.2.2). IgG was purified from 35 ml of culture supernate of each by protein G chromatography (NB70p44). Neither purified mAb specifically reacted with hPMS2-134 expressed in CHO.

A second round of fusion, using mouse #480, and screening was initiated (NB70p48). Seventeen hybridomas were selected (based on their reactivity towards bacterially expressed hPMS2-134 by the Yaciuk group) and tested for reactivity towards CHO-expressed hPMS2-134. None displayed specific reactivity towards hPMS2-134. Screening against bacterial hPMS2-134 was repeated. Four hybridomas (349-22, 349-25, 349-29, 349-36) were reactive (NB70p52).

Deletion studies pointed to the originally isolated mAbs (349-1.1.3 and 349-1.2.2) sharing an epitope C-terminal to residue 81, while second generation mAbs shared epitopes located between amino acids 55 and 81. Epitope mapping studies using overlapping 15-mer peptides failed to identify relevant epitopes.

Second generation hybridomas (from mouse #480) were subcloned by limiting dilution twice. Culture supernatants were tested for reactivity towards bacterial hPMS2-134. The majority displayed reactivity by Western blotting (NB71p7). Of these, clones 349-22.1.3 and 349-29.5.2 were selected for expansion. Further validation was performed. Horseradish peroxidase (HRP) conjugation to 349-29.5.2 was conducted, and the results of a Western blot probed with supernatant fluid from clone 349-29.5.2 and with HRP-conjugated 349-29.5.2 antibody is shown in FIG. 1. Each well contained increasing amounts of a human cell line expressing PMS2-134. The wells shown contained 30,000; 60,000; 90,000; and 120,000 cells/well in lanes 1, 2, 3, and 4, respectively.

What is claimed is:

1. An isolated monoclonal antibody that specifically binds to an epitope located between amino acids 55 and 81 of SEQ ID NO:1.

2. The antibody of claim 1 wherein said antibody is conjugated to a detectable label.

3. The antibody of claim 2 wherein said label is an enzyme, biotin, a radionuclide, a fluorophore, a chemiluminescer, or a paramagnetic particle.

4. An isolated antibody-producing cell that produces the antibody of claim 1.

5. An isolated monoclonal antibody that specifically binds to an epitope located between amino acids 81 and 133 of SEQ ID NO:1.

6. The antibody of claim 5 wherein said antibody is conjugated to a detectable label.

7. The antibody of claim 6 wherein said label is an enzyme, biotin, a radionuclide, a fluorophore, a chemiluminescer, or a paramagnetic particle.

8. An isolated antibody-producing cell that produces the antibody of claim 5.

* * * * *

SEQUENCE LISTING

```
<160> NUMBER OF SEQ ID NOS: 6

<210> SEQ ID NO 1
<211> LENGTH: 133
<212> TYPE: PRT
<213> ORGANISM: Homo sapiens

<400> SEQUENCE: 1

Met Glu Arg Ala Glu Ser Ser Ser Thr Glu Pro Ala Lys Ala Ile Lys
1               5                   10                  15

Pro Ile Asp Arg Lys Ser Val His Gln Ile Cys Ser Gly Gln Val Val
            20                  25                  30

Leu Ser Leu Ser Thr Ala Val Lys Glu Leu Val Glu Asn Ser Leu Asp
        35                  40                  45

Ala Gly Ala Thr Asn Ile Asp Leu Lys Leu Lys Asp Tyr Gly Val Asp
    50                  55                  60

Leu Ile Glu Val Ser Asp Asn Gly Cys Gly Val Glu Glu Glu Asn Phe
65                  70                  75                  80

Glu Gly Leu Thr Leu Lys His His Thr Ser Lys Ile Gln Glu Phe Ala
                85                  90                  95

Asp Leu Thr Gln Val Glu Thr Phe Gly Phe Arg Gly Glu Ala Leu Ser
            100                 105                 110

Ser Leu Cys Ala Leu Ser Asp Val Thr Ile Ser Thr Cys His Ala Ser
        115                 120                 125

Ala Lys Val Gly Thr
    130

<210> SEQ ID NO 2
<211> LENGTH: 862
<212> TYPE: PRT
<213> ORGANISM: Homo sapiens

<400> SEQUENCE: 2

Met Glu Arg Ala Glu Ser Ser Ser Thr Glu Pro Ala Lys Ala Ile Lys
1               5                   10                  15

Pro Ile Asp Arg Lys Ser Val His Gln Ile Cys Ser Gly Gln Val Val
            20                  25                  30
```

-continued

Leu Ser Leu Ser Thr Ala Val Lys Glu Leu Val Glu Asn Ser Leu Asp
         35                  40                  45

Ala Gly Ala Thr Asn Ile Asp Leu Lys Leu Lys Asp Tyr Gly Val Asp
         50                  55                  60

Leu Ile Glu Val Ser Asp Asn Gly Cys Gly Val Glu Glu Glu Asn Phe
65                   70                  75                  80

Glu Gly Leu Thr Leu Lys His His Thr Ser Lys Ile Gln Glu Phe Ala
             85                  90                  95

Asp Leu Thr Gln Val Glu Thr Phe Gly Phe Arg Gly Glu Ala Leu Ser
             100                 105                 110

Ser Leu Cys Ala Leu Ser Asp Val Thr Ile Ser Thr Cys His Ala Ser
             115                 120                 125

Ala Lys Val Gly Thr Arg Leu Met Phe Asp His Asn Gly Lys Ile Ile
             130                 135                 140

Gln Lys Thr Pro Tyr Pro Arg Pro Arg Gly Thr Thr Val Ser Val Gln
145                 150                 155                 160

Gln Leu Phe Ser Thr Leu Pro Val Arg His Lys Glu Phe Gln Arg Asn
             165                 170                 175

Ile Lys Lys Glu Tyr Ala Lys Met Val Gln Val Leu His Ala Tyr Cys
             180                 185                 190

Ile Ile Ser Ala Gly Ile Arg Val Ser Cys Thr Asn Gln Leu Gly Gln
             195                 200                 205

Gly Lys Arg Gln Pro Val Val Cys Thr Gly Gly Ser Pro Ser Ile Lys
             210                 215                 220

Glu Asn Ile Gly Ser Val Phe Gly Gln Lys Gln Leu Gln Ser Leu Ile
225                 230                 235                 240

Pro Phe Val Gln Leu Pro Pro Ser Asp Ser Val Cys Glu Glu Tyr Gly
             245                 250                 255

Leu Ser Cys Ser Asp Ala Leu His Asn Leu Phe Tyr Ile Ser Gly Phe
             260                 265                 270

Ile Ser Gln Cys Thr His Gly Val Gly Arg Ser Ser Thr Asp Arg Gln
             275                 280                 285

Phe Phe Phe Ile Asn Arg Arg Pro Cys Asp Pro Ala Lys Val Cys Arg
             290                 295                 300

Leu Val Asn Glu Val Tyr His Met Tyr Asn Arg His Gln Tyr Pro Phe
305                 310                 315                 320

Val Val Leu Asn Ile Ser Val Asp Ser Glu Cys Val Asp Ile Asn Val
             325                 330                 335

Thr Pro Asp Lys Arg Gln Ile Leu Leu Gln Glu Glu Lys Leu Leu Leu
             340                 345                 350

Ala Val Leu Lys Thr Ser Leu Ile Gly Met Phe Asp Ser Asp Val Asn
             355                 360                 365

Lys Leu Asn Val Ser Gln Gln Pro Leu Leu Asp Val Glu Gly Asn Leu
             370                 375                 380

Ile Lys Met His Ala Ala Asp Leu Glu Lys Pro Met Val Glu Lys Gln
385                 390                 395                 400

Asp Gln Ser Pro Ser Leu Arg Thr Gly Glu Lys Lys Asp Val Ser
             405                 410                 415

Ile Ser Arg Leu Arg Glu Ala Phe Ser Leu Arg His Thr Thr Glu Asn
             420                 425                 430

Lys Pro His Ser Pro Lys Thr Pro Glu Pro Arg Arg Ser Pro Leu Gly
             435                 440                 445

-continued

```
Gln Lys Arg Gly Met Leu Ser Ser Thr Ser Gly Ala Ile Ser Asp
    450                 455                 460
Lys Gly Val Leu Arg Pro Gln Lys Glu Ala Val Ser Ser Ser His Gly
465                 470                 475                 480
Pro Ser Asp Pro Thr Asp Arg Ala Glu Val Glu Lys Asp Ser Gly His
                485                 490                 495
Gly Ser Thr Ser Val Asp Ser Glu Gly Phe Ser Ile Pro Asp Thr Gly
            500                 505                 510
Ser His Cys Ser Ser Glu Tyr Ala Ala Ser Ser Pro Gly Asp Arg Gly
        515                 520                 525
Ser Gln Glu His Val Asp Ser Gln Glu Lys Ala Pro Glu Thr Asp Asp
    530                 535                 540
Ser Phe Ser Asp Val Asp Cys His Ser Asn Gln Glu Asp Thr Gly Cys
545                 550                 555                 560
Lys Phe Arg Val Leu Pro Gln Pro Thr Asn Leu Ala Thr Pro Asn Thr
                565                 570                 575
Lys Arg Phe Lys Lys Glu Glu Ile Leu Ser Ser Ser Asp Ile Cys Gln
            580                 585                 590
Lys Leu Val Asn Thr Gln Asp Met Ser Ala Ser Gln Val Asp Val Ala
        595                 600                 605
Val Lys Ile Asn Lys Lys Val Val Pro Leu Asp Phe Ser Met Ser Ser
    610                 615                 620
Leu Ala Lys Arg Ile Lys Gln Leu His His Glu Ala Gln Gln Ser Glu
625                 630                 635                 640
Gly Glu Gln Asn Tyr Arg Lys Phe Arg Ala Lys Ile Cys Pro Gly Glu
                645                 650                 655
Asn Gln Ala Ala Glu Asp Glu Leu Arg Lys Glu Ile Ser Lys Thr Met
            660                 665                 670
Phe Ala Glu Met Glu Ile Ile Gly Gln Phe Asn Leu Gly Phe Ile Ile
        675                 680                 685
Thr Lys Leu Asn Glu Asp Ile Phe Ile Val Asp Gln His Ala Thr Asp
    690                 695                 700
Glu Lys Tyr Asn Phe Glu Met Leu Gln Gln His Thr Val Leu Gln Gly
705                 710                 715                 720
Gln Arg Leu Ile Ala Pro Gln Thr Leu Asn Leu Thr Ala Val Asn Glu
                725                 730                 735
Ala Val Leu Ile Glu Asn Leu Glu Ile Phe Arg Lys Asn Gly Phe Asp
            740                 745                 750
Phe Val Ile Asp Glu Asn Ala Pro Val Thr Glu Arg Ala Lys Leu Ile
        755                 760                 765
Ser Leu Pro Thr Ser Lys Asn Trp Thr Phe Gly Pro Gln Asp Val Asp
    770                 775                 780
Glu Leu Ile Phe Met Leu Ser Asp Ser Pro Gly Val Met Cys Arg Pro
785                 790                 795                 800
Ser Arg Val Lys Gln Met Phe Ala Ser Arg Ala Cys Arg Lys Ser Val
                805                 810                 815
Met Ile Gly Thr Ala Leu Asn Thr Ser Glu Met Lys Lys Leu Ile Thr
            820                 825                 830
His Met Gly Glu Met Asp His Pro Trp Asn Cys Pro His Gly Arg Pro
        835                 840                 845
Thr Met Arg His Ile Ala Asn Leu Gly Val Ile Ser Gln Asn
    850                 855                 860
```

```
<210> SEQ ID NO 3
<211> LENGTH: 16
<212> TYPE: PRT
<213> ORGANISM: Homo sapiens

<400> SEQUENCE: 3

Ile Gln Glu Phe Ala Asp Leu Thr Gln Val Glu Thr Phe Gly Phe Arg
1               5                   10                  15

<210> SEQ ID NO 4
<211> LENGTH: 17
<212> TYPE: PRT
<213> ORGANISM: Homo sapiens

<400> SEQUENCE: 4

Glu Leu Val Glu Asn Ser Leu Asp Ala Gly Ala Thr Asn Ile Asp Leu
1               5                   10                  15

Lys

<210> SEQ ID NO 5
<211> LENGTH: 859
<212> TYPE: PRT
<213> ORGANISM: Mus musculus

<400> SEQUENCE: 5

Met Glu Gln Thr Glu Gly Val Ser Thr Glu Cys Ala Lys Ala Ile Lys
1               5                   10                  15

Pro Ile Asp Gly Lys Ser Val His Gln Ile Cys Ser Gly Gln Val Ile
                20                  25                  30

Leu Ser Leu Ser Thr Ala Val Lys Glu Leu Ile Glu Asn Ser Val Asp
            35                  40                  45

Ala Gly Ala Thr Thr Ile Asp Leu Arg Leu Lys Asp Tyr Gly Val Asp
        50                  55                  60

Leu Ile Glu Val Ser Asp Asn Gly Cys Gly Val Glu Glu Glu Asn Phe
65                  70                  75                  80

Glu Gly Leu Ala Leu Lys His His Thr Ser Lys Ile Gln Glu Phe Ala
                85                  90                  95

Asp Leu Thr Gln Val Glu Thr Phe Gly Phe Arg Gly Glu Ala Leu Ser
            100                 105                 110

Ser Leu Cys Ala Leu Ser Asp Val Thr Ile Ser Thr Cys His Gly Ser
        115                 120                 125

Ala Ser Val Gly Thr Arg Leu Val Phe Asp His Asn Gly Lys Ile Thr
    130                 135                 140

Gln Lys Thr Pro Tyr Pro Arg Pro Lys Gly Thr Thr Val Ser Val Gln
145                 150                 155                 160

His Leu Phe Tyr Thr Leu Pro Val Arg Tyr Lys Glu Phe Gln Arg Asn
                165                 170                 175

Ile Lys Lys Glu Tyr Ser Lys Met Val Gln Val Leu Gln Ala Tyr Cys
            180                 185                 190

Ile Ile Ser Ala Gly Val Arg Val Ser Cys Thr Asn Gln Leu Gly Gln
        195                 200                 205

Gly Lys Arg His Ala Val Val Cys Thr Ser Gly Thr Ser Gly Met Lys
    210                 215                 220

Glu Asn Ile Gly Ser Val Phe Gly Gln Lys Gln Leu Gln Ser Leu Ile
225                 230                 235                 240

Pro Phe Val Gln Leu Pro Pro Ser Asp Ala Val Cys Glu Glu Tyr Gly
                245                 250                 255
```

-continued

```
Leu Ser Thr Ser Gly Arg His Lys Thr Phe Ser Thr Phe Arg Ala Ser
            260                 265                 270

Phe His Ser Ala Arg Thr Ala Pro Gly Gly Val Gln Gln Thr Gly Ser
        275                 280                 285

Phe Ser Ser Ile Arg Gly Pro Val Thr Gln Gln Arg Ser Leu Ser
    290                 295                 300

Leu Ser Met Arg Phe Tyr His Met Tyr Asn Arg His Gln Tyr Pro Phe
305                 310                 315                 320

Val Val Leu Asn Val Ser Val Asp Ser Glu Cys Val Asp Ile Asn Val
                325                 330                 335

Thr Pro Asp Lys Arg Gln Ile Leu Leu Gln Glu Lys Leu Leu Leu
            340                 345                 350

Ala Val Leu Lys Thr Ser Leu Ile Gly Met Phe Asp Ser Asp Ala Asn
        355                 360                 365

Lys Leu Asn Val Asn Gln Gln Pro Leu Leu Asp Val Glu Gly Asn Leu
    370                 375                 380

Val Lys Leu His Thr Ala Glu Leu Glu Lys Pro Val Pro Gly Lys Gln
385                 390                 395                 400

Asp Asn Ser Pro Ser Leu Lys Ser Thr Ala Asp Glu Lys Arg Val Ala
                405                 410                 415

Ser Ile Ser Arg Leu Arg Glu Ala Phe Ser Leu His Pro Thr Lys Glu
            420                 425                 430

Ile Lys Ser Arg Gly Pro Glu Thr Ala Glu Leu Thr Arg Ser Phe Pro
        435                 440                 445

Ser Glu Lys Arg Gly Val Leu Ser Ser Tyr Pro Ser Asp Val Ile Ser
    450                 455                 460

Tyr Arg Gly Leu Arg Gly Ser Gln Asp Lys Leu Val Ser Pro Thr Asp
465                 470                 475                 480

Ser Pro Gly Asp Cys Met Asp Arg Glu Lys Ile Glu Lys Asp Ser Gly
                485                 490                 495

Leu Ser Ser Thr Ser Ala Gly Ser Glu Glu Phe Ser Thr Pro Glu
            500                 505                 510

Val Ala Ser Ser Phe Ser Ser Asp Tyr Asn Val Ser Ser Leu Glu Asp
        515                 520                 525

Arg Pro Ser Gln Glu Thr Ile Asn Cys Gly Asp Leu Asp Cys Arg Pro
    530                 535                 540

Pro Gly Thr Gly Gln Ser Leu Lys Pro Glu Asp His Gly Tyr Gln Cys
545                 550                 555                 560

Lys Ala Leu Pro Leu Ala Arg Leu Ser Pro Thr Asn Ala Lys Arg Phe
                565                 570                 575

Lys Thr Glu Glu Arg Pro Ser Asn Val Asn Ile Ser Gln Arg Leu Pro
            580                 585                 590

Gly Pro Gln Ser Thr Ser Ala Ala Glu Val Asp Val Ala Ile Lys Met
        595                 600                 605

Asn Lys Arg Ile Val Leu Leu Glu Phe Ser Leu Ser Ser Leu Ala Lys
    610                 615                 620

Arg Met Lys Gln Leu Gln His Leu Lys Ala Gln Asn Lys His Glu Leu
625                 630                 635                 640

Ser Tyr Arg Lys Phe Arg Ala Lys Ile Cys Pro Gly Glu Asn Gln Ala
                645                 650                 655

Ala Glu Asp Glu Leu Arg Lys Glu Ile Ser Lys Ser Met Phe Ala Glu
            660                 665                 670
```

```
Met Glu Ile Leu Gly Gln Phe Asn Leu Gly Phe Ile Val Thr Lys Leu
            675                 680                 685

Lys Glu Asp Leu Phe Leu Val Asp Gln His Ala Ala Asp Glu Lys Tyr
690                 695                 700

Asn Phe Glu Met Leu Gln Gln His Thr Val Leu Gln Ala Gln Arg Leu
705                 710                 715                 720

Ile Thr Pro Gln Thr Leu Asn Leu Thr Ala Val Asn Glu Ala Val Leu
                725                 730                 735

Ile Glu Asn Leu Glu Ile Phe Arg Lys Asn Gly Phe Asp Phe Val Ile
            740                 745                 750

Asp Glu Asp Ala Pro Val Thr Glu Arg Ala Lys Leu Ile Ser Leu Pro
        755                 760                 765

Thr Ser Lys Asn Trp Thr Phe Gly Pro Gln Asp Ile Asp Glu Leu Ile
770                 775                 780

Phe Met Leu Ser Asp Ser Pro Gly Val Met Cys Arg Pro Ser Arg Val
785                 790                 795                 800

Arg Gln Met Phe Ala Ser Arg Ala Cys Arg Lys Ser Val Met Ile Gly
                805                 810                 815

Thr Ala Leu Asn Ala Ser Glu Met Lys Lys Leu Ile Thr His Met Gly
            820                 825                 830

Glu Met Asp His Pro Trp Asn Cys Pro His Gly Arg Pro Thr Met Arg
        835                 840                 845

His Val Ala Asn Leu Asp Val Ile Ser Gln Asn
    850                 855

<210> SEQ ID NO 6
<211> LENGTH: 923
<212> TYPE: PRT
<213> ORGANISM: Arabidopsis thaliana

<400> SEQUENCE: 6

Met Gln Gly Asp Ser Ser Pro Ser Pro Thr Thr Thr Ser Ser Pro Leu
1               5                   10                  15

Ile Arg Pro Ile Asn Arg Asn Val Ile His Arg Ile Cys Ser Gly Gln
            20                  25                  30

Val Ile Leu Asp Leu Ser Ser Ala Val Lys Glu Leu Val Glu Asn Ser
        35                  40                  45

Leu Asp Ala Gly Ala Thr Ser Ile Glu Ile Asn Leu Arg Asp Tyr Gly
    50                  55                  60

Glu Asp Tyr Phe Gln Val Ile Asp Asn Gly Cys Gly Ile Ser Pro Thr
65                  70                  75                  80

Asn Phe Lys Val Leu Ala Leu Lys His His Thr Ser Lys Leu Glu Asp
                85                  90                  95

Phe Thr Asp Leu Leu Asn Leu Thr Thr Tyr Gly Phe Arg Gly Glu Ala
            100                 105                 110

Leu Ser Ser Leu Cys Ala Leu Gly Asn Leu Thr Val Glu Thr Arg Thr
        115                 120                 125

Lys Asn Glu Pro Val Ala Thr Leu Leu Thr Phe Asp His Ser Gly Leu
    130                 135                 140

Leu Thr Ala Glu Lys Lys Thr Ala Arg Gln Ile Gly Thr Thr Val Thr
145                 150                 155                 160

Val Arg Lys Leu Phe Ser Asn Leu Pro Val Arg Ser Lys Glu Phe Lys
                165                 170                 175

Arg Asn Ile Arg Lys Glu Tyr Gly Lys Leu Val Ser Leu Leu Asn Ala
            180                 185                 190
```

-continued

```
Tyr Ala Leu Ile Ala Lys Gly Val Arg Phe Val Cys Ser Asn Thr Thr
        195                 200                 205
Gly Lys Asn Pro Lys Ser Val Val Leu Asn Thr Gln Gly Arg Gly Ser
        210                 215                 220
Leu Lys Asp Asn Ile Ile Thr Val Phe Gly Ile Ser Thr Phe Thr Ser
225                 230                 235                 240
Leu Gln Pro Val Ser Ile Cys Val Ser Glu Asp Cys Arg Val Glu Gly
                245                 250                 255
Phe Leu Ser Lys Pro Gly Gln Gly Thr Gly Arg Asn Leu Ala Asp Arg
            260                 265                 270
Gln Tyr Phe Ile Asn Gly Arg Pro Val Asp Met Pro Lys Val Ser
        275                 280                 285
Lys Leu Val Asn Glu Leu Tyr Lys Asp Thr Ser Ser Arg Lys Tyr Pro
        290                 295                 300
Val Thr Ile Leu Asp Phe Ile Val Pro Gly Gly Ala Cys Asp Leu Asn
305                 310                 315                 320
Val Thr Pro Asp Lys Arg Lys Val Phe Phe Ser Asp Glu Thr Ser Val
                325                 330                 335
Ile Gly Ser Leu Arg Glu Gly Leu Asn Glu Ile Tyr Ser Ser Ser Asn
            340                 345                 350
Ala Ser Tyr Ile Val Asn Arg Phe Glu Glu Asn Ser Glu Gln Pro Asp
        355                 360                 365
Lys Ala Gly Val Ser Ser Phe Gln Lys Lys Ser Asn Leu Leu Ser Glu
        370                 375                 380
Gly Ile Val Leu Asp Val Ser Ser Lys Thr Arg Leu Gly Glu Ala Ile
385                 390                 395                 400
Glu Lys Glu Asn Pro Ser Leu Arg Glu Val Glu Ile Asp Asn Ser Ser
                405                 410                 415
Pro Met Glu Lys Phe Lys Phe Glu Ile Lys Ala Cys Gly Thr Lys Lys
            420                 425                 430
Gly Glu Gly Ser Leu Ser Val His Asp Val Thr His Leu Asp Lys Thr
        435                 440                 445
Pro Ser Lys Gly Leu Pro Gln Leu Asn Val Thr Glu Lys Val Thr Asp
        450                 455                 460
Ala Ser Lys Asp Leu Ser Ser Arg Ser Ser Phe Ala Gln Ser Thr Leu
465                 470                 475                 480
Asn Thr Phe Val Thr Met Gly Lys Arg Lys His Glu Asn Ile Ser Thr
                485                 490                 495
Ile Leu Ser Glu Thr Pro Val Leu Arg Asn Gln Thr Ser Ser Tyr Arg
            500                 505                 510
Val Glu Lys Ser Lys Phe Glu Val Arg Ala Leu Ala Ser Arg Cys Leu
        515                 520                 525
Val Glu Gly Asp Gln Leu Asp Asp Met Val Ile Ser Lys Glu Asp Met
        530                 535                 540
Thr Pro Ser Glu Arg Asp Ser Glu Leu Gly Asn Arg Ile Ser Pro Gly
545                 550                 555                 560
Thr Gln Ala Asp Asn Val Glu Arg His Glu Arg Glu His Glu Lys Pro
                565                 570                 575
Ile Arg Phe Glu Glu Pro Thr Ser Asp Asn Thr Leu Thr Lys Gly Asp
            580                 585                 590
Val Glu Arg Val Ser Glu Asp Asn Pro Arg Cys Ser Gln Pro Leu Arg
        595                 600                 605
```

```
                                       -continued
Ser Val Ala Thr Val Leu Asp Ser Pro Ala Gln Ser Thr Gly Pro Lys
        610                 615                 620

Met Phe Ser Thr Leu Glu Phe Ser Phe Gln Asn Leu Arg Thr Arg Arg
625                     630                 635                 640

Leu Glu Arg Leu Ser Arg Leu Gln Ser Thr Gly Tyr Val Ser Lys Cys
                645                 650                     655

Met Asn Thr Pro Gln Pro Lys Lys Cys Phe Ala Ala Ala Thr Leu Glu
            660             665                     670

Leu Ser Gln Pro Asp Asp Glu Glu Arg Lys Ala Arg Ala Leu Ala Ala
        675                 680                 685

Ala Thr Ser Glu Leu Glu Arg Leu Phe Arg Lys Glu Asp Phe Arg Arg
        690             695                 700

Met Gln Val Leu Gly Gln Phe Asn Leu Gly Phe Ile Ile Ala Lys Leu
705                 710                 715                     720

Glu Arg Asp Leu Phe Ile Val Asp Gln His Ala Ala Asp Glu Lys Phe
                725                 730                 735

Asn Phe Glu His Leu Ala Arg Ser Thr Val Leu Asn Gln Gln Pro Leu
            740                 745                 750

Leu Gln Pro Leu Asn Leu Glu Leu Ser Pro Glu Glu Val Thr Val
        755                 760                 765

Leu Met His Met Asp Ile Ile Arg Glu Asn Gly Phe Leu Leu Glu Glu
770                 775                 780

Asn Pro Ser Ala Pro Pro Gly Lys His Phe Arg Leu Arg Ala Ile Pro
785                 790                 795                 800

Tyr Ser Lys Asn Ile Thr Phe Gly Val Glu Asp Leu Lys Asp Leu Ile
            805                 810                     815

Ser Thr Leu Gly Asp Asn His Gly Glu Cys Ser Val Ala Ser Ser Tyr
            820             825                 830

Lys Thr Ser Lys Thr Asp Ser Ile Cys Pro Ser Arg Val Arg Ala Met
        835                 840                 845

Leu Ala Ser Arg Ala Cys Arg Ser Ser Val Met Ile Gly Asp Pro Leu
    850                 855                 860

Arg Lys Asn Glu Met Gln Lys Ile Val Glu His Leu Ala Asp Leu Glu
865                 870                 875                 880

Ser Pro Trp Asn Cys Pro His Gly Arg Pro Thr Met Arg His Leu Val
            885                 890                     895

Asp Leu Thr Thr Leu Leu Thr Leu Pro Asp Asp Asn Val Asn Asp
            900                 905                 910

Asp Asp Asp Asp Asp Ala Thr Ile Ser Leu Ala
            915                 920
```